US012635894B2

(12) United States Patent
Ben Ishay et al.

(10) Patent No.:    US 12,635,894 B2
(45) Date of Patent:        May 26, 2026

(54) SENSOR DEVICE TO MITIGATE THE EFFECTS OF UNWANTED SIGNALS MADE IN OPTICAL MEASUREMENTS OF BIOLOGICAL PROPERTIES

(71) Applicant: BIOBEAT TECHNOLOGIES LTD., Petach Tikva (IL)

(72) Inventors: Arik Ben Ishay, Zoran (IL); Israel Sarussi, Ganei Tal (IL); Johanan May, Petach Tikva (IL)

(73) Assignee: BIOBEAT TECHNOLOGIES LTD., Petach Tikva (IL)

(*) Notice: Subject to any disclaimer, the term of this patent is extended or adjusted under 35 U.S.C. 154(b) by 261 days.

(21) Appl. No.: 16/898,461

(22) Filed: Jun. 11, 2020

(65) Prior Publication Data

US 2021/0386308 A1     Dec. 16, 2021

(51) Int. Cl.
*A61B 5/024*        (2006.01)
*A61B 5/00*         (2006.01)
(Continued)

(52) U.S. Cl.
CPC ........ *A61B 5/02427* (2013.01); *A61B 5/0064* (2013.01); *A61B 5/02028* (2013.01);
(Continued)

(58) Field of Classification Search
CPC .............. A61B 5/02427; A61B 5/0064; A61B 5/02028; A61B 5/021; A61B 5/0816;
(Continued)

(56) References Cited

U.S. PATENT DOCUMENTS

| 3,973,129 A | 8/1976 | Blumberg et al. |
| 4,703,758 A | 11/1987 | Omura et al. |
| | (Continued) | |

FOREIGN PATENT DOCUMENTS

| CN | 104000572 | 8/2014 |
| CN | 203885491 | 10/2014 |
| | (Continued) | |

OTHER PUBLICATIONS

An Office Action dated Apr. 1, 2019, which issued during the prosecution of U.S. Appl. No. 15/218,123.
(Continued)

*Primary Examiner* — Abid A Mustansir
(74) *Attorney, Agent, or Firm* — Sughrue Mion, PLLC

(57)        ABSTRACT

A method for a wearable device to determine a biological parameter of a tissue of a person. To apply an emitting of a first and a second wavelength of light towards the tissue. To collect and sense a first and a second set of frequency bands from the signals received back from the first and the second wavelengths, respectively. The first set of frequency bands represents a first signal which corresponds to a combination of the biological parameter and an extraneous noise. The second set of frequency bands represents a second signal mainly comprising the extraneous noise. To subtract the first set of frequency bands from the second set of frequency bands in the frequency domain to obtain a third set of frequency bands. The third set of frequency bands represents a third signal corresponding to the biological parameter.

20 Claims, 8 Drawing Sheets

(51) Int. Cl.

| | |
|---|---|
| *A61B 5/02* | (2006.01) |
| *A61B 5/021* | (2006.01) |
| *A61B 5/08* | (2006.01) |
| *A61B 5/145* | (2006.01) |
| *A61B 5/1455* | (2006.01) |
| *G01N 21/47* | (2006.01) |
| *G01N 21/53* | (2006.01) |

(52) U.S. Cl.
  CPC ............ *A61B 5/021* (2013.01); *A61B 5/0816* (2013.01); *A61B 5/14546* (2013.01); *A61B 5/1455* (2013.01); *A61B 5/4266* (2013.01); *A61B 5/4872* (2013.01); *A61B 5/681* (2013.01); *A61B 5/7214* (2013.01); *G01N 21/532* (2013.01); *A61B 2562/0242* (2013.01); *G01N 2021/473* (2013.01); *G01N 2201/021* (2013.01); *G01N 2201/123* (2013.01); *G01N 2201/1242* (2013.01)

(58) Field of Classification Search
  CPC . A61B 5/14546; A61B 5/1455; A61B 5/4266; A61B 5/4872; A61B 5/681; A61B 2562/0242
  See application file for complete search history.

(56) References Cited

U.S. PATENT DOCUMENTS

| | | | |
|---|---|---|---|
| 5,273,036 A | | 12/1993 | Kronberg et al. |
| 5,377,673 A | | 1/1995 | Van Dell et al. |
| 5,396,893 A | | 3/1995 | Oberg et al. |
| 5,431,170 A | * | 7/1995 | Mathews ............... A61B 5/681 |
| | | | 600/323 |
| 5,687,721 A | | 11/1997 | Kuhls et al. |
| 5,800,348 A | | 9/1998 | Kaestle |
| 5,868,671 A | | 2/1999 | Mahoney |
| 6,027,452 A | | 2/2000 | Flaherty et al. |
| 6,134,458 A | * | 10/2000 | Rosenthal ............ A61B 5/0059 |
| | | | 600/310 |
| 6,252,032 B1 | | 6/2001 | Van Antwerp et al. |
| 6,256,523 B1 | | 7/2001 | Diab |
| 6,434,420 B1 | | 8/2002 | Taheri |
| 6,491,647 B1 | | 12/2002 | Bridger et al. |
| 6,493,567 B1 | | 12/2002 | Krivitski et al. |
| 6,553,242 B1 | | 4/2003 | Sarussi |
| 6,556,851 B1 | | 4/2003 | Ott et al. |
| 6,616,613 B1 | | 9/2003 | Goodman et al. |
| 6,714,812 B1 | | 3/2004 | Karjalainen et al. |
| 6,719,705 B2 | | 4/2004 | Mills |
| 7,002,468 B2 | | 2/2006 | Eveland et al. |
| 7,003,338 B2 | | 2/2006 | Weber et al. |
| 7,006,855 B1 | | 2/2006 | Sarussi |
| 7,027,849 B2 | | 4/2006 | Al-Ali et al. |
| 7,212,850 B2 | | 5/2007 | Prystowsky et al. |
| 7,314,451 B2 | | 1/2008 | Halperin et al. |
| 7,343,186 B2 | | 3/2008 | Lamego et al. |
| 7,359,741 B2 | | 4/2008 | Sarussi |
| 7,440,787 B2 | | 10/2008 | Diab et al. |
| 7,515,948 B1 | | 4/2009 | Balberg et al. |
| 7,613,490 B2 | | 11/2009 | Sarussi et al. |
| 7,641,614 B2 | | 1/2010 | Asada et al. |
| 7,650,176 B2 | | 1/2010 | Sarussi et al. |
| 7,715,905 B2 | | 5/2010 | Kurzweil et al. |
| 7,791,155 B2 | | 9/2010 | Diab |
| 7,865,222 B2 | | 1/2011 | Weber et al. |
| 7,907,996 B2 | | 3/2011 | Prystowsky et al. |
| 7,909,768 B1 | | 3/2011 | Turcott |
| 7,941,207 B2 | | 5/2011 | Korzinov |
| 7,953,474 B2 | | 5/2011 | Hwang et al. |
| 7,996,187 B2 | | 8/2011 | Nanikashvili et al. |
| 8,055,321 B2 | | 11/2011 | Bernreuter |
| 8,180,440 B2 | | 5/2012 | McCombie et al. |
| 8,204,580 B2 | | 6/2012 | Kurzweil et al. |
| 8,233,955 B2 | | 7/2012 | Al-ali et al. |
| 8,423,106 B2 | | 4/2013 | Lamego et al. |
| 8,457,703 B2 | | 6/2013 | Al-ali et al. |
| 8,483,807 B2 | | 7/2013 | Kurzweil et al. |
| 8,548,550 B2 | | 10/2013 | Al-ali et al. |
| 8,585,607 B2 | | 11/2013 | Klap et al. |
| 8,591,411 B2 | | 11/2013 | Banet et al. |
| 8,676,286 B2 | | 3/2014 | Weber et al. |
| 8,725,226 B2 | | 5/2014 | Isaacson |
| 8,795,185 B2 | | 8/2014 | Cho |
| 8,821,418 B2 | | 9/2014 | Meger et al. |
| 8,868,149 B2 | | 10/2014 | Eisen et al. |
| 8,868,150 B2 | | 10/2014 | Al-ali et al. |
| 8,956,293 B2 | | 2/2015 | McCombie et al. |
| 8,956,294 B2 | | 2/2015 | McCombie et al. |
| 8,968,195 B2 | | 3/2015 | Tran |
| 8,983,587 B2 | | 3/2015 | Kurzweil et al. |
| 9,044,150 B2 | | 6/2015 | Brumback et al. |
| 9,049,998 B2 | | 6/2015 | Brumback et al. |
| 9,084,569 B2 | | 7/2015 | Weber et al. |
| 9,149,216 B1 | | 10/2015 | Eisen et al. |
| 9,179,851 B2 | | 11/2015 | Baumann et al. |
| 9,241,635 B2 | | 1/2016 | Yuen et al. |
| 9,314,197 B2 | | 4/2016 | Eisen et al. |
| 9,339,220 B2 | | 5/2016 | Lamego et al. |
| 9,351,671 B2 | | 5/2016 | Ruchti et al. |
| 9,442,523 B2 | | 9/2016 | Lee et al. |
| 9,449,493 B2 | | 9/2016 | Shinar et al. |
| 9,474,445 B2 | | 10/2016 | Eveland |
| 9,597,004 B2 | | 3/2017 | Hughes et al. |
| 9,642,537 B2 | | 5/2017 | Felix et al. |
| 9,730,622 B2 | | 8/2017 | Eisen et al. |
| 9,750,429 B1 | | 9/2017 | Sackner et al. |
| 9,770,213 B2 | | 9/2017 | Kirenko et al. |
| 9,775,534 B2 | | 10/2017 | Korzinov et al. |
| 9,801,547 B2 | | 10/2017 | Yuen et al. |
| 9,801,588 B2 | | 10/2017 | Weber et al. |
| 9,883,809 B2 | | 2/2018 | Klap et al. |
| 9,952,095 B1 | | 4/2018 | Hotelling et al. |
| 9,955,887 B2 | | 5/2018 | Hughes et al. |
| 10,078,052 B2 | | 9/2018 | Ness et al. |
| 10,206,589 B2 | | 2/2019 | Walker et al. |
| 10,219,754 B1 | | 3/2019 | Lamego |
| 10,247,670 B2 | | 4/2019 | Ness et al. |
| 10,258,265 B1 | | 4/2019 | Poeze et al. |
| 10,258,266 B1 | | 4/2019 | Poeze et al. |
| 10,278,645 B2 | | 5/2019 | Moon |
| 10,292,625 B2 | | 5/2019 | Shinar et al. |
| 10,299,708 B1 | | 5/2019 | Poeze et al. |
| 10,368,772 B2 | | 8/2019 | Banet et al. |
| 10,376,190 B1 | | 8/2019 | Poeze et al. |
| 10,376,191 B1 | | 8/2019 | Poeze et al. |
| 10,420,493 B2 | | 9/2019 | Al-ali et al. |
| 10,470,695 B2 | | 11/2019 | Al-ali |
| 10,524,671 B2 | | 1/2020 | Lamego |
| 10,536,768 B2 | | 1/2020 | Wagner |
| 10,660,520 B2 | | 5/2020 | Lin |
| 10,786,211 B2 | | 9/2020 | Halperin et al. |
| 10,806,351 B2 | | 10/2020 | Moon et al. |
| 10,813,562 B2 | | 10/2020 | Moon et al. |
| 10,813,578 B1 | | 10/2020 | Ben Ishay et al. |
| 10,856,752 B2 | | 12/2020 | Banet et al. |
| 11,009,390 B2 | | 5/2021 | Hotelling et al. |
| 11,241,177 B2 | | 2/2022 | Eisen et al. |
| 2002/0044279 A1 | | 4/2002 | Khoury et al. |
| 2002/0099277 A1 | | 7/2002 | Harry et al. |
| 2003/0149349 A1 | | 8/2003 | Jensen |
| 2003/0220549 A1 | | 11/2003 | Liu et al. |
| 2003/0233036 A1 | | 12/2003 | Ansari et al. |
| 2004/0030258 A1 | | 2/2004 | Williams et al. |
| 2004/0092822 A1 | | 5/2004 | Robinson et al. |
| 2004/0111035 A1 | | 6/2004 | Kondoh et al. |
| 2004/0158240 A1 | | 8/2004 | Avrahami |
| 2004/0183997 A1 | | 9/2004 | Suzuki |
| 2005/0002031 A1 | | 1/2005 | Kraemer et al. |
| 2005/0075549 A1 | | 4/2005 | Kondoh et al. |
| 2005/0096513 A1 | | 5/2005 | Ozguz et al. |
| 2005/0113661 A1 | | 5/2005 | Nazeri et al. |
| 2006/0079789 A1 | | 4/2006 | Lee et al. |
| 2006/0094941 A1 | | 5/2006 | Cho et al. |

(56)  References Cited

U.S. PATENT DOCUMENTS

| | | |
|---|---|---|
| 2006/0151709 A1 | 7/2006 | Hahl |
| 2007/0000374 A1 | 1/2007 | Clark et al. |
| 2007/0038050 A1 | 2/2007 | Sarussi |
| 2007/0118054 A1 | 5/2007 | Pinhas et al. |
| 2007/0213607 A1 | 9/2007 | Mandelis et al. |
| 2008/0114260 A1 | 5/2008 | Lange et al. |
| 2008/0139953 A1 | 6/2008 | Baker et al. |
| 2008/0288026 A1 | 11/2008 | Cross et al. |
| 2009/0018421 A1 | 1/2009 | Sarussi et al. |
| 2009/0116017 A1 | 5/2009 | Xu et al. |
| 2010/0036265 A1 | 2/2010 | Kim et al. |
| 2010/0049018 A1 | 2/2010 | Duffy |
| 2010/0056887 A1* | 3/2010 | Kimura .............. A61B 5/14552 |
| | | 600/324 |
| 2010/0081913 A1 | 4/2010 | Cross et al. |
| 2010/0105996 A1 | 4/2010 | Segman |
| 2010/0130840 A1 | 5/2010 | Isaacson |
| 2010/0137779 A1 | 6/2010 | Seitz |
| 2010/0256518 A1 | 10/2010 | Yu et al. |
| 2010/0276733 A1 | 11/2010 | Li |
| 2011/0152694 A1 | 6/2011 | Shimoyama et al. |
| 2011/0230773 A1 | 9/2011 | Ting et al. |
| 2012/0009126 A1 | 1/2012 | Singaram et al. |
| 2012/0132211 A1 | 5/2012 | Halperin et al. |
| 2012/0143067 A1 | 6/2012 | Watson et al. |
| 2012/0253142 A1 | 10/2012 | Meger et al. |
| 2012/0283535 A1 | 11/2012 | Sarussi |
| 2013/0137998 A1 | 5/2013 | Lange et al. |
| 2013/0245389 A1 | 9/2013 | Schultz et al. |
| 2013/0267791 A1 | 10/2013 | Halperin et al. |
| 2013/0281866 A1 | 10/2013 | Shinar et al. |
| 2013/0296674 A1 | 11/2013 | Watson et al. |
| 2013/0324860 A1 | 12/2013 | Borgos et al. |
| 2014/0051946 A1 | 2/2014 | Arne et al. |
| 2014/0058272 A1 | 2/2014 | Naing et al. |
| 2014/0275852 A1 | 9/2014 | Hong et al. |
| 2015/0036133 A1 | 2/2015 | Uematsu et al. |
| 2015/0087932 A1 | 3/2015 | Halperin et al. |
| 2015/0094552 A1 | 4/2015 | Golda et al. |
| 2015/0250390 A1 | 9/2015 | Murray |
| 2015/0276589 A1 | 10/2015 | Wagner et al. |
| 2015/0327792 A1 | 11/2015 | Shinar et al. |
| 2015/0351690 A1 | 12/2015 | Toth et al. |
| 2015/0366469 A1 | 12/2015 | Harris et al. |
| 2015/0374255 A1 | 12/2015 | Vasapollo |
| 2016/0058428 A1 | 3/2016 | Shinar et al. |
| 2016/0061726 A1 | 3/2016 | Ness et al. |
| 2016/0183818 A1* | 6/2016 | Richards ............ A61B 5/02433 |
| | | 600/479 |
| 2016/0192716 A1 | 7/2016 | Lee |
| 2016/0192868 A1 | 7/2016 | Levant et al. |
| 2016/0192884 A1 | 7/2016 | Levant et al. |
| 2016/0228049 A1 | 8/2016 | Nackaerts et al. |
| 2017/0014056 A1 | 1/2017 | Newberry |
| 2017/0020399 A1 | 1/2017 | Shemesh et al. |
| 2017/0055855 A1 | 3/2017 | Yoon |
| 2017/0086691 A1 | 3/2017 | Freschl et al. |
| 2017/0164848 A1 | 6/2017 | Nadeau et al. |
| 2017/0188872 A1 | 7/2017 | Hughes et al. |
| 2017/0238819 A1 | 8/2017 | Waller et al. |
| 2017/0281017 A1 | 10/2017 | Halperin et al. |
| 2017/0292908 A1 | 10/2017 | Wilk et al. |
| 2017/0305132 A1 | 10/2017 | Dollase et al. |
| 2017/0325698 A1 | 11/2017 | Allec et al. |
| 2017/0347894 A1 | 12/2017 | Bhushan et al. |
| 2018/0000362 A1 | 1/2018 | Matsuo et al. |
| 2018/0020960 A1* | 1/2018 | Sarussi .............. G01N 33/4925 |
| | | 600/310 |
| 2018/0042496 A1 | 2/2018 | Lachhman et al. |
| 2018/0146870 A1 | 5/2018 | Shemesh et al. |
| 2018/0146877 A1 | 5/2018 | Baker et al. |
| 2018/0168504 A1 | 6/2018 | Ding et al. |
| 2018/0303353 A1 | 10/2018 | Baxi et al. |
| 2018/0317852 A1* | 11/2018 | MacDonald ......... A61B 5/7246 |
| 2019/0059752 A1 | 2/2019 | Botsva et al. |
| 2019/0083044 A1 | 3/2019 | Halperin et al. |
| 2019/0090860 A1 | 3/2019 | Shinar et al. |
| 2020/0185107 A1 | 6/2020 | Cox et al. |
| 2020/0214579 A1 | 7/2020 | Phillips et al. |
| 2020/0281523 A1 | 9/2020 | Maidel et al. |
| 2020/0367760 A1 | 11/2020 | Klaassen et al. |
| 2021/0100489 A1 | 4/2021 | Katz et al. |
| 2021/0361171 A1 | 11/2021 | Valent et al. |

FOREIGN PATENT DOCUMENTS

| | | |
|---|---|---|
| CN | 104605835 | 5/2015 |
| CN | 105943005 | 9/2016 |
| CN | 206558105 | 10/2017 |
| CN | 107411702 | 12/2017 |
| DE | 4446390 | 7/1996 |
| DE | 102011101934 | 11/2012 |
| EP | 0144509 | 6/1985 |
| EP | 0443267 | 8/1991 |
| EP | 1520514 | 4/2005 |
| EP | 1139865 | 10/2007 |
| EP | 1936356 | 6/2008 |
| EP | 2270516 | 1/2011 |
| EP | 3033992 | 6/2016 |
| FR | 2105327 | 4/1972 |
| GB | 2357846 | 7/2001 |
| JP | 2004113434 | 4/2004 |
| JP | 2009168670 | 7/2009 |
| JP | 2013068461 | 4/2013 |
| JP | 2014117503 | 6/2014 |
| JP | 2014130046 | 7/2014 |
| KR | 100756654 | 9/2007 |
| KR | 20080044223 | 8/2008 |
| KR | 20130065513 | 6/2013 |
| KR | 101490445 | 2/2015 |
| KR | 20170064906 | 6/2017 |
| WO | 89/11825 | 12/1989 |
| WO | 92/07511 | 5/1992 |
| WO | 96/39922 | 12/1996 |
| WO | 99/63883 | 12/1999 |
| WO | 00/22982 | 4/2000 |
| WO | 00/43536 | 7/2000 |
| WO | 00/60350 | 10/2000 |
| WO | 01/17421 | 3/2001 |
| WO | 01/43624 | 6/2001 |
| WO | 01/53806 | 7/2001 |
| WO | 01/60248 | 8/2001 |
| WO | 01/94938 | 12/2001 |
| WO | 03/025562 | 3/2003 |
| WO | 03/096876 | 11/2003 |
| WO | 2004/090786 | 10/2004 |
| WO | 2009/047774 | 4/2009 |
| WO | 2016/115369 | 7/2016 |
| WO | 2016/168090 | 10/2016 |
| WO | 2016/178119 | 11/2016 |
| WO | 2017/004129 | 1/2017 |
| WO | 2017/115343 | 7/2017 |
| WO | 2018/013656 | 1/2018 |
| WO | 2018/020492 | 2/2018 |
| WO | 2018/069931 | 4/2018 |
| WO | 2018/202824 | 11/2018 |
| WO | 2019/172570 | 9/2019 |
| WO | 2020/095296 | 5/2020 |
| WO | 2021/130749 | 7/2021 |

OTHER PUBLICATIONS

An Office Action dated Sep. 11, 2018, which issued during the prosecution of U.S. Appl. No. 15/218,123.

Torres Filho, Ivo P., James Terner, and Linda Scheider. "Resonance Raman spectroscopy of human sickle cell hemoglobin from transgenic mice." The FASEB Journal 23 (2009): 768-2.—Abstract.

Hayes, Matthew J., and Peter R. Smith. "Artifact reduction in photoplethysmography." Applied Optics 37.31 (1998): 7437-7446.

Wauschkuhn, Constantin A., et al. "Circadian periodicity of cerebral blood flow revealed by laser-Doppler flowmetry in awake rats: relation to blood pressure and activity." American Journal of Physi-

(56)                References Cited

OTHER PUBLICATIONS ology—Heart and Circulatory Physiology 289.4 (2005): H1662-H1668.

Draghici, Adina E., et al. "Functional Near Infrared Spectroscopy for Measuring Bone Hemoglobin Content after Excercise in Individuals with Spinal Cord Injury."—Conference Abstract.

U.S. Appl. No. 62/758,642, filed Nov. 11, 2018.

An Office Action dated Apr. 6, 2022, which issued during the prosecution of U.S. Appl. No. 17/327,799.

An Office Action dated July 6. 2022, which issued during the prosecution of U.S. Appl. No. 17/327,799.

An Office Action dated Sep. 17, 2021, which issued during the prosecution of U.S. Appl. No. 17/327,799.

Byrom, Bill, et al. "A review evaluating the validity of smartphone sensors and components to measure clinical outcomes in clinical research." Value in Health 19.3 (2016): A72.

Zirk, K., H. Pötzschke, and W. K. R. Barnikol. "Ein miniaturisierbares, sehr empfindliches Polarimeter als Detektor einer implantierbaren Glukosesonde. II. Opto-elektronische Verstärkung und Verarbeitung der Meßsignale—A Miniaturisable Highly Sensitive Polarimeter for Use as a Detector in an Implantable Glucose Probe. II. Opto-electronic Amplification and Processing of Measuring Signals." (2001): 262-272.—Full article in German and English Abstract.

Abay, T. Y., and P. A. Kyriacou. "Comparison of NIRS, laser Doppler flowmetry, photoplethysmography, and pulse oximetry during vascular occlusion challenges." Physiological Measurement 37.4 (2016): 503.—ABstract.

Sakota, Daisuke, and Setsuo Takatani. "Plasma surface reflectance spectroscopy for non-invasive and continuous monitoring of extracellular component of blood." Optical Sensing and Detection II. vol. 8439. SPIE, 2012.—Abstract.

An Office Action dated Mar. 6, 2020, which issued during the prosecution of U.S. Appl. No. 16/726,976.

Wolf, Martin, et al. "Detection of the fast neuronal signal on the motor cortex using functional frequency domain near infrared spectroscopy." Oxygen Transport to Tissue XXIII. Springer, Boston, MA, 2003. 193-197.—Abstract.

An International Search Report and a Written Opinion both dated Oct. 22, 2017, which issued during the prosecution of Applicant's PCT/IL2017/050752.

Mozaffarieh, Maneli, et al. "Relationship between optic nerve head and finger blood flow." European journal of ophthalmology 20.1 (2010): 136-141.—Abstract.

Nogawa, Masamichi, et al. "New hybrid reflectance optical pulse oximetry sensor for lower oxygen saturation measurement and for broader clinical application." Biomedical Sensing, Imaging, and Tracking Technologies II. vol. 2976. SPIE, 1997.

Petrig, B. L., and L. Follonier. "New ray tracing model for the estimation of power spectral properties in laser Doppler velocimetry of retinal vessels." Investigative Ophthalmology & Visual Science 46.13 (2005): 4290-4290.—Abstract.

An International Search Report and a Written Opinion both dated Feb. 16, 2020, which issued during the prosecution of Applicant's PCT/IL2019/051204.

European Search Report dated Dec. 11. 2019 which issued during the prosecution of Applicant's European App No. 17833695.4.

An International Search Report and a Written Opinion both dated Mar. 25, 2021, which issued during the prosecution of Applicant's PCT/IL2020/051314.

Villanueva, Rachel, et al. "Effect of peripheral perfusion on accuracy of pulse oximetry in children." Journal of clinical anesthesia 11.4 (1999): 317-322.—Abstract.

European Search Report dated Jul. 21, 2022 which issued during the prosecution of Applicant's European App No. 19881827.0.

An International Search Report and a Written Opinion both dated Aug. 31, 2022, which issued during the prosecution of Applicant's PCT/IL2022/050531.

Larsen, Vagn H., Theis Hansen, and Steen L. Nielsen. "Oxygen status determined by the photo-electric method—a circular finger-probe constructed for detection of blood oxygen content, blood flow and vascular density." Scandinavian Journal of Clinical and Laboratory Investigation 53.sup214 (1993): 75-81.

Maattala, Miia, et al. "Optimum place for measuring pulse oximeter signal in wireless sensor-belt or wrist-band." 2007 International Conference on Convergence Information Technology (ICCIT 2007). IEEE, 2007.

Vacas-Jacques, Paulino, et al. "Development and validation of a physiological tag for monitoring oxygen saturation in muscle of free-diving whales." Lasers in Surgery and Medicine. vol. 44. Commerce Place, 350 Main St, Malden 02148, MA USA: Wiley-Blackwell, 2012.—Abstract.

Lu, Xiuling, et al. "Disuccinimidyl suberate cross-linked hemoglobin as a novel red blood cell substitute." Science in China. Series C, Life Sciences 48.1 (2005): 49-60.—Abstract.

Myllylä, Teemu S., et al. "Fibre optic sensor for non-invasive monitoring of blood pressure during MRI scanning." Journal of biophotonics 4.1-2 (2011): 98-107.—Abstract.

Physics and Technology of Emitters and Detectors, Vishay Telefunken, Dec. 1999, p. 11-24.

Harja, Juha, Teemu S. Myllylä, and Risto A. Myllylä. "MRI-compatible noninvasive continuous blood pressure measurement using fiber optics." Saratov Fall Meeting 2009: International School for Junior Scientists and Students on Optics, Laser Physics, and Biophotonics. vol. 7547. SPIE, 2010.—Abstract.

Lee, Hwansung, and Yoshiyuki Taenaka. "Hydrodynamic characteristics of the Edwards MIRA bileaflet valve in a pneumatic ventricular assist device." ASAIO Journal 53.4 (2007): 397-402.

Adam, N., and P. Ghosh. "Hyaluronan molecular weight and polydispersity in some commercial intra-articular injectable preparations and in synovial fluid." Inflammation Research 50.6 (2001): 294-299.—Abstract.

An Office Action together with an English Summary dated Aug. 17, 2021 which issued during the prosecution of Chinese Patent Application No. 201780057511.9.

An Office Action together with an English Summary dated Jan. 22, 2021 which issued during the prosecution of Chinese Patent Application No. 201780057511.9.

Download of scientific diagram from researchgate.com—downloaded on Jun. 10, 2022.

Nie, Baoqing, et al. "Droplet-based interfacial capacitive sensing." Lab on a Chip 12.6 (2012): 1110-1118.—Abstract.

An Office Action together with an English Summary dated Feb. 25, 2022 which issued during the prosecution of Chinese Patent Application No. 201780057511.9.

An International Search Report and a Written Opinion both dated Jul. 25, 2021, which issued during the prosecution of Applicant's PCT/IL2021/050711.

Emily Emilsson: "Time of Flight Spectroscopy in human muscle tissue", Department of Atomic Physics, Lund University, Jun. 2, 2015.

Office Action issued Jul. 18, 2023 in U.S. Appl. No. 17/327,718.

Office Action issued Aug. 15, 2023 in U.S. Appl. No. 17/412,570.

European Search Report dated Sep. 29, 2023 which issued during the prosecution of Applicant's European App No. 20904745.5.

Office Action issued Apr. 26, 2024 in U.S. Appl. No. 17/274,841.

* cited by examiner 610                    615

620                    625

630                    635

SENSOR DEVICE TO MITIGATE THE EFFECTS OF UNWANTED SIGNALS MADE IN OPTICAL MEASUREMENTS OF BIOLOGICAL PROPERTIES

FIELD

The present invention is generally in the field of optical measurement of biological properties of an examined subject, and to an optical measurement of blood related parameters of the examined subject. In particular the present invention relates to a device to measuring certain features of optical measurement of blood detected by a detector. The device improves the signal to noise ratio by mitigation of extraneous noise of the optical measurements detected by the detector.

BACKGROUND

The majority of optical blood pulse measurements (e.g., pulse oximetry) may be carried out utilizing transmissive measurement techniques requiring sensor devices that are mountable over two opposite sides of a thin body part/organ (e.g., fingertip or earlobe). In contrast to transmissive measurement techniques, reflective measurement techniques use a light source and a light detector which are on the same side of a tissue.

There are various advantages for reflective blood measurement techniques, which may be considered to be preferable in certain applications, particularly in types of wearable medical devices, such as medical watches or patches. Some of the advantages of reflective blood measurement techniques include, among other things, the ability to conduct optical measurements on almost any part of the body, including thick organs. Other advantages may be associated with the reduced energy consumption of reflective measurement techniques. The reduced energy consumption stems from the minimal energy required to reflect light from tissue layers, as opposed to transmissive techniques where the light is required to pass through the entire width of the organ.

There may be however various limitations associated with the reflective measurement techniques, such as low signal-to-noise ratios (SNR) and low AC/DC ratios. Alternating current (AC) in the light detector as a result of the light detection of the light wave signals received from (capillary) blood vessels may originate from the heart activity. The received light signals may be reflected back from the blood vessel towards the device from which the light signal was emitted, or be transmitted via the body tissue, having the light detector placed on another side of the body tissue than the light emitter. Direct current (DC) in the light detector as a result of the light detection of the light wave signals may be a combination of light wave signals reflected from other parts of the examined organ tissue and light wave signals reflected directly from the organ surface which do not pass through the examined tissue.

Attempts to overcome limitations of reflective measurement techniques may include increasing the power of the irradiated light, by increasing the electrical current supplied to the light source and/or by increasing the number of light sources. Increasing the power of radiated light and/or increasing the number of light sources may also result in a respective increase of noise components in the measured light signals. The respective increase of noise components in the measured light signals may be due to respective increase of the baseline DC component and thus may not provide satisfying results. The increase of noise components in the measured light signals may additionally be due to movement of the sensing device attached to a user when the user is moving or exercising. There is therefore a need to improve the quality of optical signals measured by reflective blood measurements techniques, to provide higher AC/DC ratios and improve the signal-to-noise ratios of the measured light signals.

SUMMARY

The subject matter discloses a method for a wearable device to determine a biological parameter of a tissue of a person. The subject matter discloses emitting a first wavelength and a second wavelength of light towards the tissue, and collecting a first and a second signals received from the first and the second wavelengths, respectively. The first and second received signals are represented based on a set of frequency bands as elaborated below. The first set of values in the frequency bands represents a first received signal which corresponds to a combination of the biological parameter and an extraneous noise. The second set of values in the frequency bands represents a second received signal mainly comprising the extraneous noise. The subject matter also comprises subtracting the first set of values in the frequency bands from the second set of values in the frequency bands in the frequency domain to obtain a third set of values in the frequency bands. The third set of values in the frequency bands represents a third signal corresponding to the biological parameter, substantially lacking the extraneous noise.

In some cases, collecting and sensing the first and the second set of values in the frequency bands may be responsive to a delay to apply the first wavelength followed by the second wavelength of light towards the tissue. In some cases, collecting and sensing the first and the second set of values in the frequency bands may be responsive to the applying of the first wavelength and the second wavelength of light at the same time towards the tissue.

The method of the subject matter may further disclose an analysis of the third signal by a processing of the third signal. The method of the subject matter may also disclose displaying the biological parameter on a display of the wearable device responsive to the analysis of the third signal. The processing may be by a Fourier transform applied on the third signal. The extraneous noise may be generated by movement at least one of the tissue and the body of the person.

The emitting of the first and the second wavelength of light may be performed laterally in a direction away from a sensor doing the sensing. The emitting of the first and the second wavelengths of light may penetrate respective first and second depths of the tissue.

The subtracting of the first set of values in the frequency bands from the second set of values in the frequency bands in the frequency domain may be performed responsive to detection of a movement of the person and/or the tissue.

The biological parameter may be a heart rate, a respiratory rate, a peripheral capillary oxygen saturation rate (SPO2), a hemoglobin level, a perspiration level. a blood pressure, a glucose level, a bilirubin level, a stroke volume or a fat level.

The subject matter also discloses a wearable device to determine a biological parameter of a tissue of a person. The wearable device includes a processing module operatively attached to a display. The wearable device also includes a light emitter operatively connected to the processing module and configured to emit a first wavelength and a second wavelength of light towards the tissue. The wearable device also includes a light sensor operatively connected to the processing module and configured to sense a first and a second signals received from the first and the second wavelengths, respectively. The first received signal corresponding to a combination of the biological parameter and an extraneous noise and the second received signal mainly comprising the extraneous noise. The processing module is configured to convert the first received signal and the second received signal to a frequency domain, to be represented by a series of values, each value is associated with a frequency band. The first received signal is represented by a first set of values in the frequency domain and the second received signal is represented by a second set of values in the frequency domain.

In some cases, the wearable device comprises a differential amplifier having a first input and a second input connected respectively to the first signal and the second signal. The amplifier may be used to amplify the signal received via the photo diode from the body tissue and convert the received signals to analog signals.

The wearable device may further include a lens mounted to a distal end of the light emitter and configured to emit the first and the second wavelength as a collimated light towards the tissue. The collimated light may be in a direction away laterally from the light sensor towards the tissue by an offset of a lens.

The wearable device may further include a reflector disposed between the light emitter and the light sensor. The light from light emitter may be reflected by the reflector in a direction away laterally from the light sensor towards the tissue. The wearable device may further include a memory module operatively attached to the processing module, the memory module may store the first and second set of values in the frequency bands.

The emitting of the first and the second wavelength of light may be performed laterally in a direction away from the light sensor. The emitting of the first and the second wavelength of light may penetrate respective first and second depths of the tissue.

The biological parameter may be a heart rate, a respiratory rate, a peripheral capillary oxygen saturation rate (SPO2), a hemoglobin level, a perspiration level. a blood pressure, a glucose level, a bilirubin level, a stroke volume or a fat level.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which.

DETAILED DESCRIPTION

Figure 1:
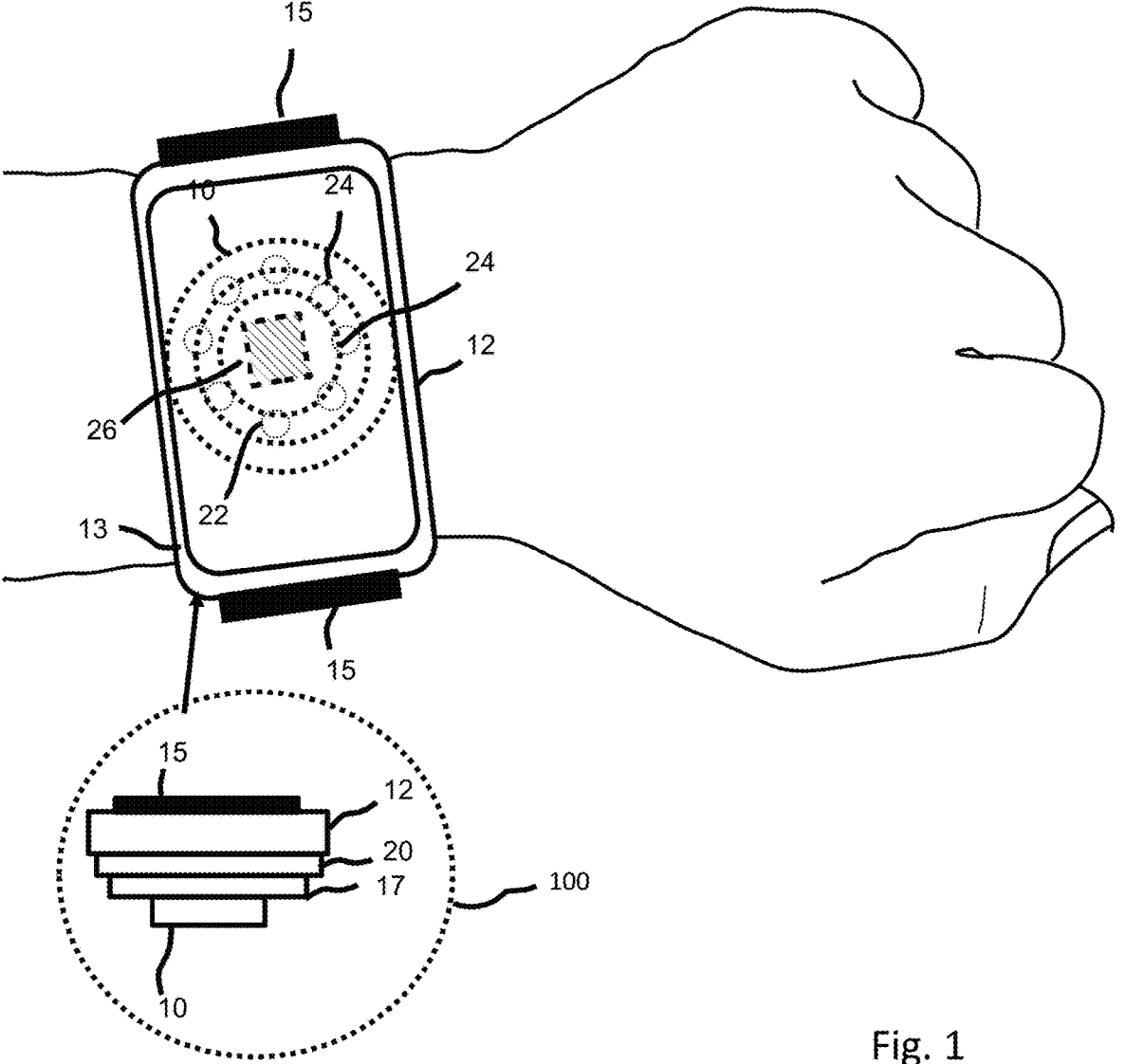
FIG. 1 shows an illustration of an application of a sensor device to an examined tissue, according to one or more illustrative aspects of the disclosure.

One or more specific embodiments of the present disclosure will be described below with reference to the drawings, which are to be considered in all aspects as illustrative only and not restrictive in any manner. In an effort to provide a concise description of these embodiments, not all features of an actual implementation are described in the specification. Elements illustrated in the drawings are not necessarily to scale, emphasis instead being placed upon clearly illustrating the principles of the invention. This invention may be provided in other specific forms and embodiments without departing from the essential characteristics described herein.

By way of introduction, the present invention discloses an optical sensor device, whereby a structure of the optical sensor device provides illumination of an examined tissue with light signals that travel laterally and away from a light detector included in the optical sensor device. Features of the structure enable received optical signals to be measured from the examined tissue with SNR and AC/DC ratios of the received optical signals to be significantly improved.

It is noted that the reflective measurement techniques and a structure of a sensor device disclosed herein are also useful for mitigation of optical signal distortions that may be induced in the measured signals of the light detector due to movements of the body part/organ to which the sensor device is attached.

The techniques disclosed herein are applicable to almost any type of optical measurements of blood properties, parameters and/or analytes, employing effects of optical absorption and scattering of electromagnetic radiation in a living tissue. Particularly, the techniques disclosed herein are useful for measuring pulsating signals, as typically obtained in types of non-invasive blood measurements, such as, but not limited to, pulse oximetry, Photoplethysmography (PPG) measurements, and the like. For example, and without being limiting, the optical measurement techniques disclosed herein may be useful for measuring blood pulses, oxygen ($O_2$) saturation, hemoglobin levels, glucose/sugar levels, bilirubin levels, and suchlike.

Reference is now made to FIG. 1, which shows an illustration of the application of a sensor device to an examined tissue, according to one or more illustrative aspects of the disclosure. Sensor device 10 is an example of a reflective optical measurement device which is illustrated in further detail below. Sensor device 10 (shown by dashed line) is located on the underside of a housing 12 so that reflectors 24 (shown by dashed line) of sensor device 10 are in contact with the skin of a wrist of a user. Other sensor devices may be placed near other users' tissues. Light emitters 22 are shown by dotted line and are configured to emit light towards the user's skin. The wearable device also comprises a light detector 26 shown by hashed lines located on the underside of housing 12. Housing 12 includes a display 13, for example being located on the housing's 12 upper surface, away from the user's skin.

The light emitters 22 may be arranged in a circle-like shape, having the light detector 26 at the center of the circle. In some other embodiments of the subject matter, the wearable device comprises multiple circles of light emitters 22 positioned concentrically to each other. Multiple circles of light emitters 22 may provide the option for illumination of the user's skin at different lateral distances away from light detector 26. Housing 12 is shown as a watch arrangement where an adjustable strap 15 is used to attach the watch to the user's wrist.

A side view 100 of the underside of a housing 12 is shown where adjustable strap 15 is attached to housing 12, substrate 20 is operatively attached inside housing 12 both mechanically and electrically and may protrude away out from housing 12 and includes connection to a battery 17. Substrate 20 includes traces (not shown) or other mechanisms which provide the electrical interconnections of the components of the sensor device 10 which require electrical power and connection, for example display 13, battery 17 and a micro control unit (MCU) (not shown). Sensor device 10 is both mechanically and electrically connected to housing 12, substrate 20 and battery 17.

Adjustable strap 15 may be tightened around the user's wrist to secure sensor device 10 onto a part of the user's body. The body part may be an ankle or around a torso of the person. Adjustable strap 15 may enable a biological property of an examined tissue of the person who is currently exercising or is monitored over a long period of time. The biological property may include heart rate, oxygen saturation, hemoglobin level, blood pressure, cardiac output, stroke volume, perspiration, glucose/sugar level, bilirubin level and fat level for example. The biological property may be displayed on display 13.

Figure 2A:
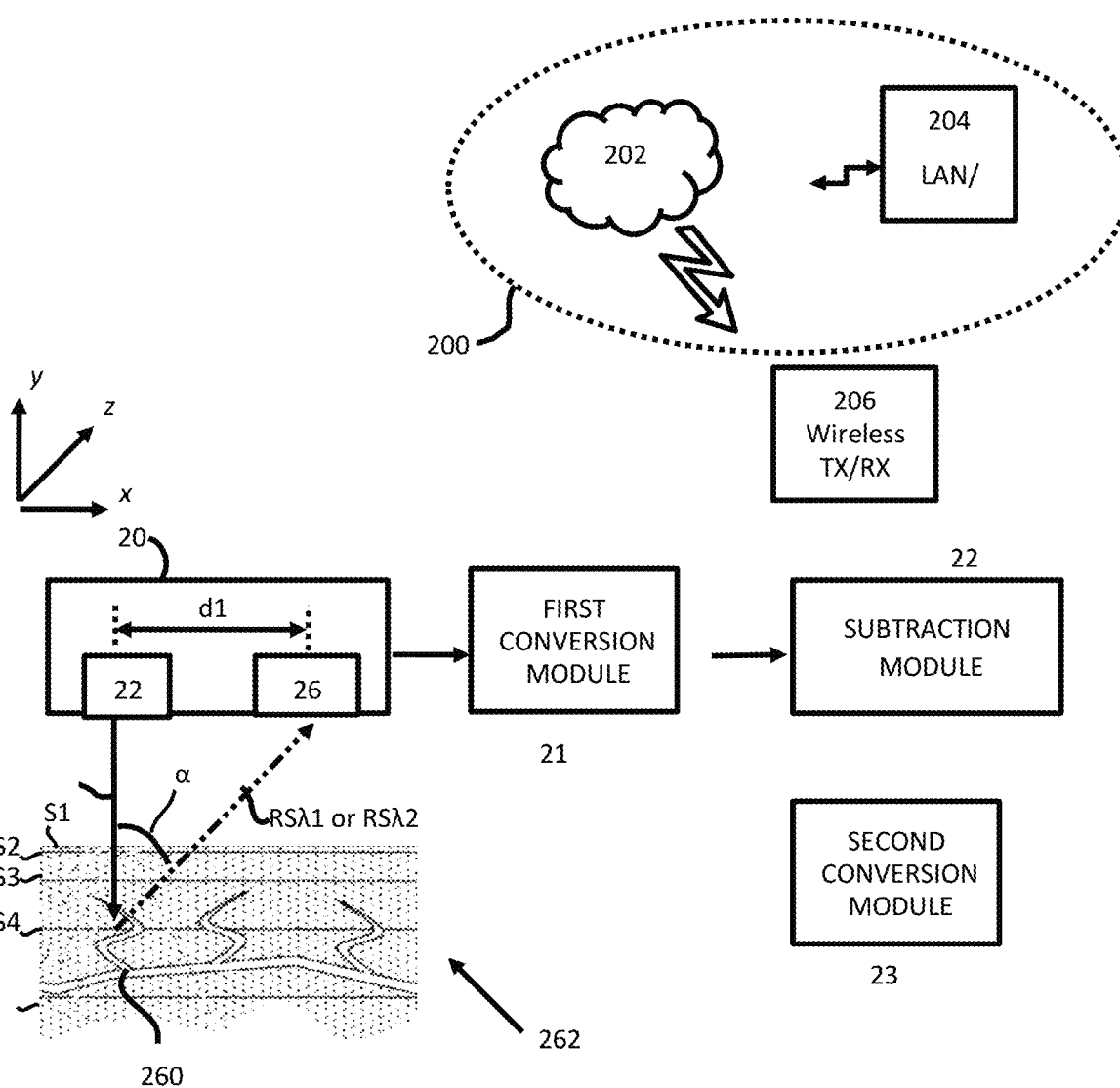
FIG. 2A shows a partial system block diagram and a positional location of a substrate relative to a tissue sample, according to one or more illustrative aspects of the disclosure.

Reference is now made to FIG. 2A which shows a partial system block diagram and a positional location of substrate 20 relative to a tissue 262, according to one or more illustrative aspects of the disclosure. As shown in FIG. 1, substrate 20 may provide a mechanical attachment of multiple reflectors 24, light emitters 22 and light detector 26 to substrate 20. The multiple reflectors 24 may be in contact with the skin of tissue 262. FIG. 2A shows an example of a deployment of sensor 10 without reflectors 24. In contrast to FIG. 1, light emitters 22 and light detector 26 are shown embedded below the surface of substrate 20.

Additional components may be included and interconnected in or connected to substrate 20. The additional components may include driver circuitries utilized to set current levels, light intensities and wavelengths of the light signals $S\lambda1$ or $S\lambda2$ emitted from light emitters 22. Light emitters 22, by way of non-limiting example, may be multicolor light emitting diodes (LEDs). Multicolor LEDs typically have three selectable wavelengths of red light (wavelength[$\lambda$]$\approx$670 nano-meters[nm]), blue ($\lambda\approx$460 nm) and green ($\lambda\approx$550 nm). Received light wave signals $RS\lambda1$ or $RS\lambda2$ having an angle $\alpha$ from the parts of tissue 262 may be a combination of light wave signals received from the tissue layers S1-S5 of tissue 262.

Alternating current (AC) in light detector 26 is a result of a light detection of the light wave signals $RS\lambda1$ or $RS\lambda2$ received from (capillary) blood vessels 260 from remote perfused tissue layers, S3, S4 and S5. The light detection may therefore originate from the heart activity of a person wearing sensor device 10. Direct current (DC) in light detector 26 may be measured as a result of the light detection of the light wave signals $RS\lambda1$ or $RS\lambda1$ received directly from near-surface tissue layers S1 and S2 which form the epidermis of the skin. Direct current (DC) in light detector 26 may also include light detection of the light wave signals $RS\lambda1$ or $RS\lambda1$ received from remote perfused tissue layers, S3, S4 and S5.

The received signals $RS\lambda1$ or $RS\lambda2$ are inputted into a first conversion module 21 that converts the received signals $RS\lambda1$ or $RS\lambda2$ into the frequency domain. Such conversion may be implemented by applying a Fourier transform on the received signals $RS\lambda1$ or $RS\lambda2$ or via any other conversion to the frequency domain desired by a person skilled in the art. The output of the first conversion module 21 comprises a set of values associated with multiple frequency bands. For example, the entire set of values may be in the range of 0-10 Hertz. In that range, there may be 20 frequency bands, each band of 0.5 Hertz. The values associated with all the frequency bands represent the output of the conversion of the received signals $RS\lambda1$ or $RS\lambda2$ into the frequency domain. The two sets of values, one for each of the received signals, which are outputted by the first conversion module 21 may be stored in predefined memory addresses in the device used for determining the physical properties of the person, for example a wearable watch.

The device also comprises a subtraction module 22 configured to subtract one set of values from the other. The first set of values represents values of the first signal in the multiple frequency bands while the second set of values represents values of the second signal in the multiple frequency bands. The subtraction is defined by subtracting the values associated with each frequency band. For example, subtracting the value of $RS\lambda1$ in the fifth band from the value of $RS\lambda2$ in the fifth band to compute the signal itself, without the noise generated by movement of the person. The output of the subtraction module 22 comprises a set of values in the multiple frequency bands which represents the signal without the noise created due to the person's movement.

The device also comprises a second conversion module 23 configured to convert the output of the subtraction module 22 from the frequency domain into the time domain. The time domain representation may show a sinusoidal signal, which lacks the noise created due to the person's movement. The second conversion module 23 may output the time domain representation of the signal, without the noise component, to a predefined memory address in the device.

Figure 5:
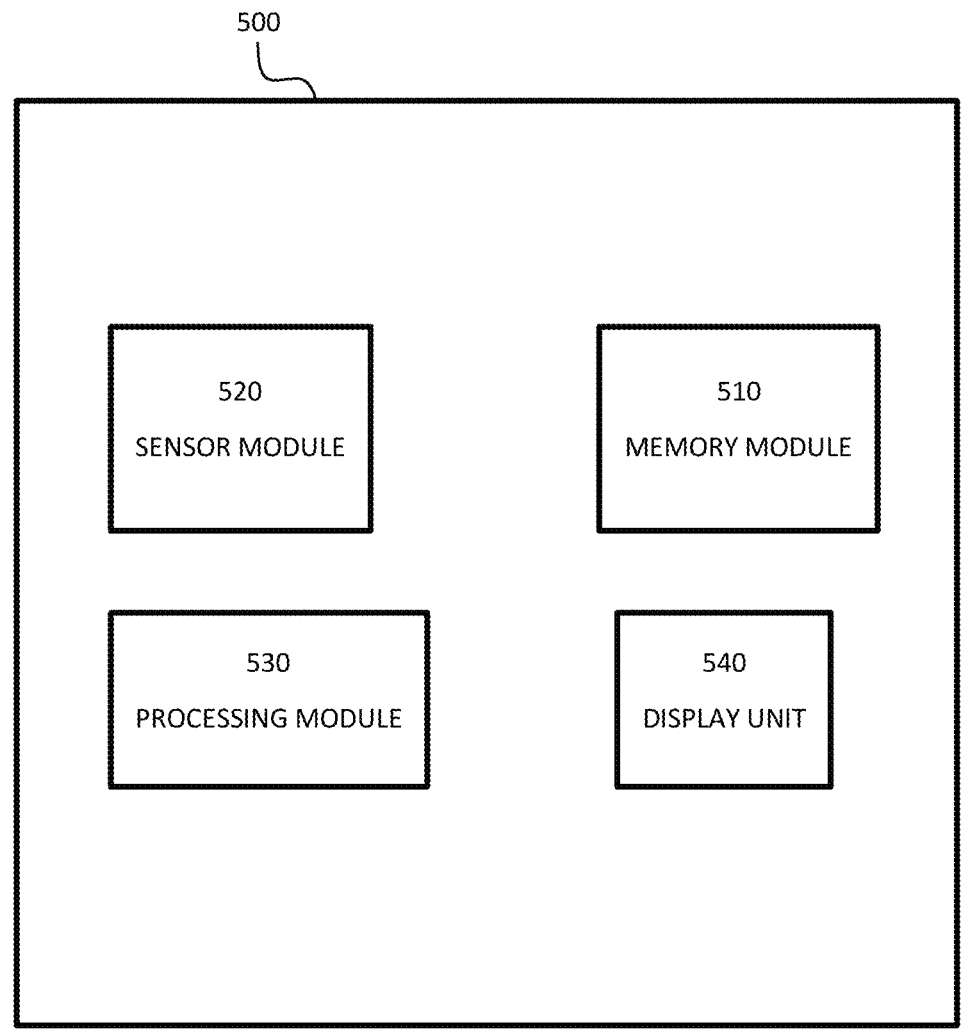
FIG. 5 shows a schematic representation for a device for extracting a biological parameter of a tissue of a person, according to one or more illustrative aspects of the disclosure.

Circuit may connect between substrate 20 and electrical components elaborated in FIG. 5. Circuit may include a differential amplifier which receives voltages and currents representative of light signal $RS\lambda1$ on its non-inverting input and voltages and currents representative of light signal $RS\lambda2$ on its inverting input via delay line DL1. Delay DL1 is utilized where light signals $S\lambda1$ or $S\lambda2$ are applied one after the other. The delay of delay DL1 and the bias of differential amplifier allows difference amplifier to perform a subtraction of light signal $RS\lambda1$ from light signal $RS\lambda2$. The subtraction may be useful to obtain more of the AC in light detector 26 as resulting light signal $RS\lambda3$. Light signal $RS\lambda1$ relates to the heart activity of a person wearing sensor device and is the major part of light signal $RS\lambda1$ since respective emitted light signal S1 penetrates tissues layers S3, S4 and S5 more deeply than light signal $S\lambda2$ does. The subtraction of light signal $RS\lambda1$ from light signal $RS\lambda2$ is therefore aimed at subtracting the DC detected included in signal $RS\lambda1$ from the combination of AC and DC of signal $RS\lambda2$.

The subtraction may also be used to mitigate the effects of an unwanted signal component included and in common to light signals RSλ1 and RSλ1. The unwanted signal component may be referred to as an extraneous noise. The extraneous noise may due to a displacement in the positional location of substrate 20 relative to the tissue 262 as referenced with respect to cartesian co-ordinates x, y and z. The displacement of the substrate on the user's skin may be caused by movement of the body or a limb of a person wearing the sensor device 10 when walking or running. The displacement of substrate 20 on the user's skin may also include localized movement of tissue 262 as a result of flexing a muscle.

Circuit may include other analogue circuitry, for example a lock-in amplifiers with phase sensitive detection properties. The phase sensitive detection properties may be utilized just on light signal RSλ1 to eliminate extraneous noise signals at frequencies other than the fundamental frequency component of light signal RSλ1. The resulting light signal RSλ3 may then be processed to display a biological property such as heart rate, oxygen saturation, hemoglobin level, blood pressure, cardiac output, stroke volume, perspiration, glucose/sugar level, bilirubin level and fat level for example.

Figure 2B:
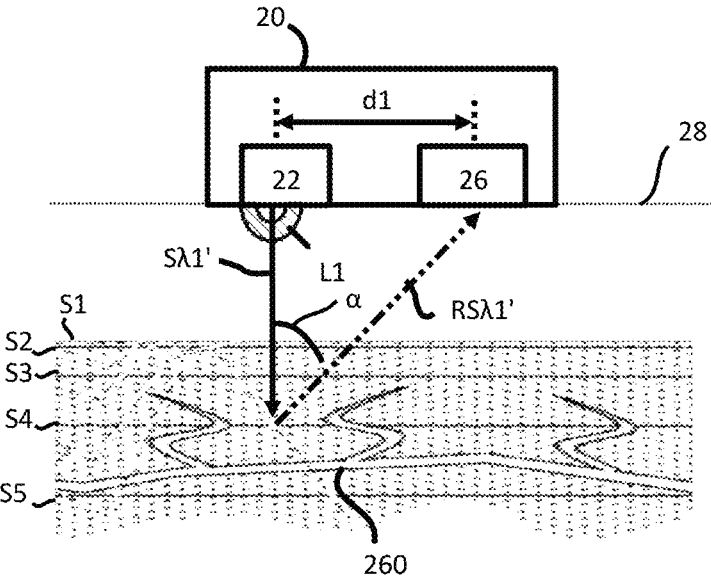
FIG. 2B shows an implementation of a substrate, according to one or more illustrative aspects of the disclosure.

Reference is now made to FIG. 2B which shows an implementation of substrate 20, according to one or more illustrative aspects of the disclosure. Substrate 20 is the same as the substrate 20 in FIG. 2A, with the addition of lens L1 which is placed on a distal end of light emitter 22. Light signals Sλ1 or Sλ2 are emitted from light emitter 22 at an angle substantially perpendicular to a first planar surface of substrate 20. The first planar surface of substrate 20 is indicated by dotted line 28. Lens L1 provides collimated light signals Sλ1' or Sλ2' to be outputted towards the user's tissue 262, as opposed to scattered light signals Sλ1 or Sλ2 shown in FIG. 2A. Lens L1 may also include a polarizing filter (not shown) which polarizes collimated light signals Sλ1' or Sλ2'. Received light wave signals RSλ1' or RSλ1' are reflected towards light detector 26 at an angle α from layers S1-S5 of tissue 262. Received light wave signals RSλ1' or RSλ1' may carry both DC and AC components when detected in light detector 26. Received light wave signals Sλ1' or Sλ1' received at angle α from the tissue layers S1-S5 of tissue 262 have signal properties that depend on parameters such as the wavelengths of light signals emitted from light emitter 22 with or without lens L1, properties of the lens L1, distance d1 between the light emitter 22 and the light detector 26, a displacement in the positional location of substrate 20 relative to a tissue 262, movement properties of a person wearing sensor device 10 and the like.

Figure 2C:
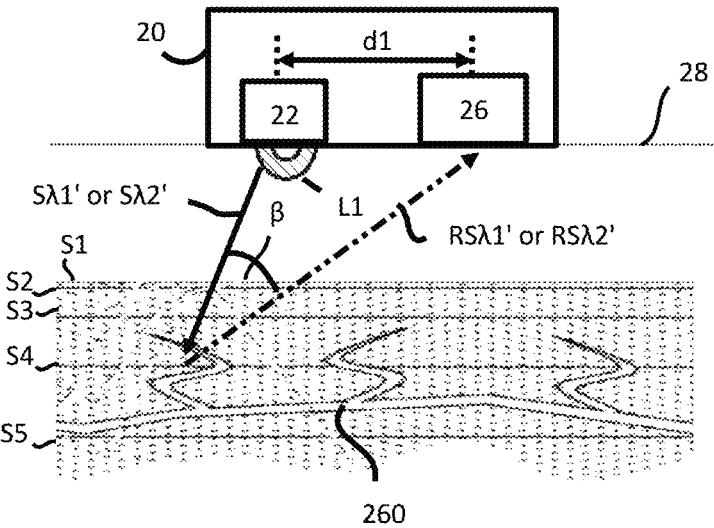
FIG. 2C shows an implementation of a substrate, according to one or more illustrative aspects of the disclosure.

Reference is now made to FIG. 2C which shows an implementation of substrate 20, according to one or more illustrative aspects of the disclosure. FIG. 2C is the same as FIG. 2A with respect to substrate 20, having an addition of lens L1 which is placed on a distal end of light emitter 22 and offset laterally towards light detector 26. Light signals are emitted from light emitter 22 at an angle substantially perpendicular to a first planar surface of substrate 20. The first planar surface of substrate 20 is indicated by dotted line 28. However, lens L1 causes light signals Sλ1' or Sλ2' to be deflected away from light detector 26 by virtue of lens L1 laterally offsetting the light signals towards light detector 26. Lens L1 provides collimated light signals Sλ1' or Sλ2' as opposed to scattered light signals Sλ1 or Sλ2 shown in FIG. 2A. Received light wave signals RSλ1' or RSλ1' received from tissue 262 towards light detector 26 are at an angle β from layers S1-S5 of tissue 262. Compared to FIG. 2B, angle β is likely to be more acute than angle α and the distance away from light detector 26 where light signals Sλ1' or Sλ2' are received in tissue 262 is much greater than where light signals Sλ1 or Sλ2 are received from tissue 262.

Lens L1 may also include a polarizing filter (not shown) which polarizes collimated light signals Sλ1' or Sλ2'. Utilization of offset lens L1 here eliminates the use of a reflector 24 to direct light signals away from light detector 26. Therefore, sensor device 10 may include multiple light emitters 22 and respective lenses L1 without any reflectors 24. Another embodiment discloses the sensor device 10 having a combination of light emitters 22 and reflectors 24, light emitters 22/lenses L1 and reflectors 24, or light emitters 22/lenses L1 and no reflectors 24.

Figure 2D:
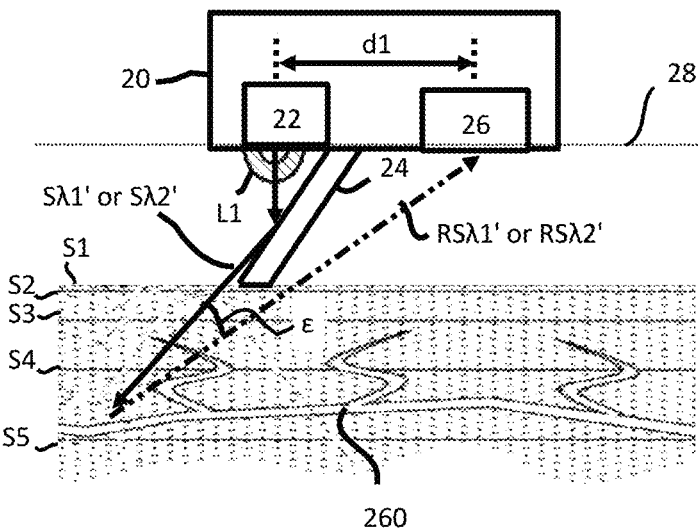
FIG. 2D shows an implementation of a substrate, according to one or more illustrative aspects of the disclosure.

Reference is now made to FIG. 2D which shows an implementation of substrate 20, according to one or more illustrative aspects of the disclosure. Similar to FIG. 2B, lens L1 is placed on a distal end of light emitter 22. Light is emitted from light emitter 22 at an angle substantially perpendicular to a first planar surface of substrate 20 (shown by dotted line 28). However, the embodiment shown in FIG. 2D includes a reflector 24 mounted to substrate 20 between light detector 26 and light emitter 22. Light is emitted from light emitter 22 and is received off reflector 24 as light signals Sλ1' or Sλ2'. Light signals Sλ1' or Sλ2' then penetrate into tissue 262 away from light detector 26 and are received from tissue layers S1-S5 towards light detector 26 at an angle ε. By comparison angle ε is likely to be more acute than angles β and α. Light signals Sλ1' or Sλ2' penetrate into tissue 262 away at a greater distance from light detector 26 than as shown in preceding FIGS. 2B-2C. The more acute angle ε and the greater distance may also permit a deeper penetration into tissue 262.

Figure 3:
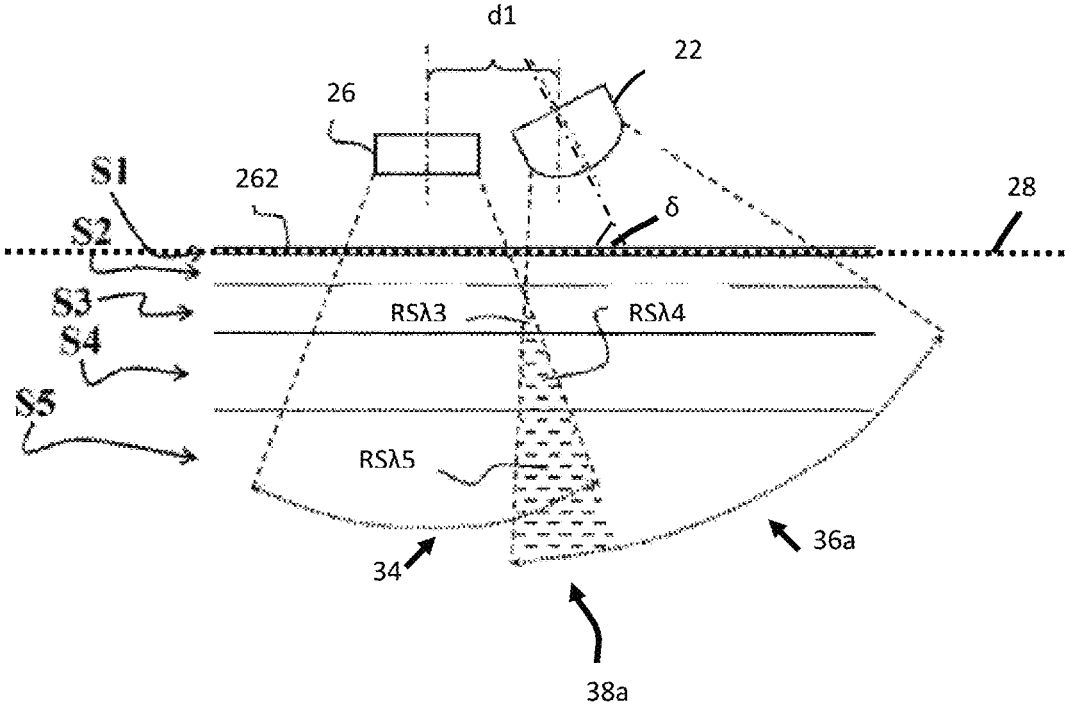
FIG. 3 illustrate features of an area of light interaction in perfused tissue layers, according to one or more illustrative aspects of the disclosure.

Reference is now made to FIG. 3 which illustrates features of an area of light interaction in perfused tissue layers S1-S5, according to one or more illustrative aspects of the disclosure. Area 38a (shown shaded) includes intersection of illumination sector 36a with perfused layers S3-S5 that coincides within a portion of sector 34. Illumination sector 36a is formed by light signals Sλ1, Sλ1' or Sλ2, Sλ2' (not shown) which may be reflected off reflector 24 and/or directed by offset lens L1 into tissue 262. Light signals RSλ3, RSλ4 and RSλ5 are reflected towards light detector 26 from respective perfused tissue layers S3, S4 and S5. The field of view of reception of received light signals of light detector 26 is indicated by sector 34. Light intersection area 38a in perfused tissue layers S3, S4 and S5 is therefore dependent on angle α relative to dashed line 28, so that light components RSλ3, RSλ4 and RSλ5 are reflected towards light detector 26 from perfused tissue layers S3, S4 and S5.

Accordingly, the baseline DC components in the optical signals measured by the light detector 26 in the reflective measurement are substantially reduced, by reducing the amount (or altogether excluding) of light components RSλ1 and RSλ2 (not shown), received from respective non-perfused tissue layers S1 and S2. On the other hand, since the optical paths, of the light components RSλ3, RSλ4 and RSλ5 received towards the light detector 26 from the perfused tissue layers are increased by virtue of angle S. The light components RSλ3, RSλ4 and RSλ5 indicate a more intense interaction with perfused tissue layers S3, S4 and S5. Thus, light components RSλ3, RSλ4 and RSλ5 may contain significantly more blood related information from pulsating blood vessels 260 and contribute greater amounts of pulsating AC components to the optical signals captured and measured by light detector 26.

US 12,635,894 B2

9

Figure 4:
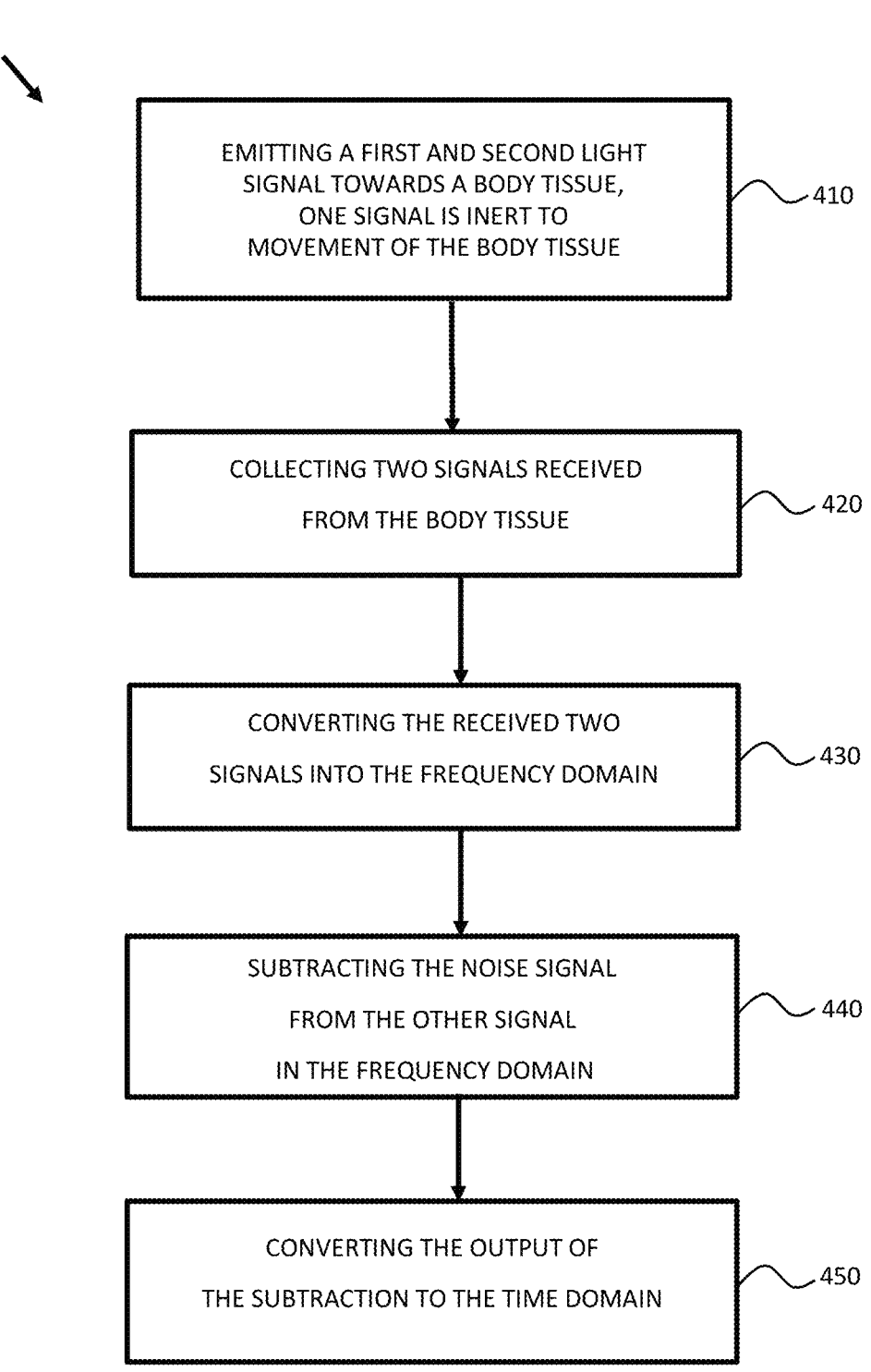
FIG. 4 shows a method for measuring and processing light signals received from blood tissues, according to one or more illustrative aspects of the disclosure.

Reference is now made to FIG. 4 which shows a method for measuring and processing light signals received from blood vessels, according to one or more illustrative aspects of the disclosure. Step 410 discloses emitting light signals from a light emitter 26 of the sensor device 10. The light signals comprise at least two signals, a first signal in a predefined wavelength to include the blood measurements combined with noise, and a second light signal meant to include noise only. The second signal is inert to changes in blood vessels of the tissue to which the light signal is emitted. The second signal may be emitted in wavelength of 1440 nano-meter.

For ease of explanation in the description which follows, the first and second signal emitted towards the user's tissue may be defined as light signals SλI and Sλ2, respectively. Light signals SλI and Sλ2 may pass through one or more components, such as a reflector, lens and the like, as described above. Circuit may include sample and hold circuitry with analogue to digital converters (ADCs) to give a binary digital representation of a series of values associated with specific frequency bands of received light signals RSλ1 and RSλ2. By way of non-limiting example, a reference is now made to the measure of pulse rate which may be derived from blood vessels 260. The reference applies to the descriptions which follow.

When a light signal enters the body tissue, it is scattered in all directions or bounced around by blood cells and other structures (blood vessels 260) in tissue 262. The light may either be absorbed into the tissue, or reflect from near-surface tissue layers S1 and S2 which form the epidermis of the skin. Hemoglobin, an oxygen-carrying protein in red blood cells, absorbs lots of blue light ($\lambda$=460 nano-meters [nm]) and reflects lots of red light ($\lambda$=670 nm). Veins such as blood vessels 260, unlike arteries carry deoxygenated blood, the deoxygenated blood absorbs more red light than the oxygen rich blood in the tissue around the vein. When the blood in veins has unloaded its oxygen to the body's cells exchanging the oxygen (O2) for carbon dioxide CO2, the blood returns to the lungs to replenish the supply of oxygen. Arteries are oxygen rich because this blood has just traveled from the lungs where it picked up oxygen inhaled from the air to the heart where is then pumped throughout the body to deliver its oxygen to the body's cells. Use of shorter wavelengths ($\lambda$) such as green light ($\lambda$=550 nm) and blue light which is mainly absorbed and received from near-surface tissue layers S1 and S2 to sense the condition of jaundice because of increased levels of bilirubin or melanin.

With respect to the emitting of light signals Sλ1 and Sλ2 in step 410, the processing module disclosed below may determine chooses which light emitter 22 to be used to emit light signals Sλ1 and Sλ2 towards tissue 262. With reference the measure of pulse rate which may be derived from blood vessels 260, light signals Sλ1 and Sλ2 are set at wavelengths respectively which do and do not absorb in the blood of tissue 262. For pulse measurement light signal Sλ1 has a red wavelength and light signal Sλ2 has a wavelength of 1440 nm.

At step 420, two light signals are received from the body tissue. The two light signals are collected by light detector 26 as a result of light signals Sλ1 and Sλ2 emitted according to step 410 and received from tissue layers S1-S5 as respective received light signals RSλ1 and RSλ2. Since light signals Sλ1 and Sλ2 are set at wavelengths which do and do not absorb in the blood of tissue 262, respective received light signals RSλ1 and RSλ2 will have different levels of absorption and different depths of absorption in tissue 262. With reference the measure of pulse rate, the movement of blood vessel 260 will cause both direct current and an alternating current to be collected and measured by light detector 26 from received light signal RSλ1. Whereas, with respect to received light signal RSλ2, there will be less alternating current (AC) collected and measured by light detector 26 and a slight increase or the same level of direct current (DC) collected and measured by light detector 26.

At step 430, the conversion module of the device which performs the process converts the first received signal and the second received signal from the time domain to the frequency domain. The converted signals may carry information sampled for at least one (1) second. In some other cases, the received signals contain information sampled for a duration in the range of 1-10 seconds. The output of the conversion to the frequency domain may be represented as two series of values associated with frequency bands. The first series of values is of the first received signal and the second series of values is of the second received signal. circuit 20 may include sample and hold circuitry with analogue to digital converters (ADCs) which allows a binary digital representation of received light signal RSλ1 and received light signal RSλ2 in the frequency domain. The binary digital representation of received light signal RSλ1 and received light signal RSλ2 in the frequency domain may be streamed via wireless transceiver 206 to cloud 202 and/or Server 204. Server 204 may be located in a LAN. The server may perform subtraction step 440. Alternatively, or in addition, memory module may be utilized by the processing module to perform subtraction step 440. The received light signal RSλ1 and received light signal RSλ2 are represented in the frequency domain as a series of values, each value in the series of values is associated with a frequency band. For example, 0.5 in the frequency band of 10 Hz, 0.3 in the frequency band of 20 Hz, 0 in the frequency band of 30 Hz, 2.1 in the frequency band of 40 Hz and the like.

In step 440, the received signal RSλ2 is subtracted from received signal RSλ1 in the frequency domain. That is, each value in a frequency band is subtracted separately. For example, in case there are 10 frequency bands, each of the received signals received RSλ2 and RSλ1 are represented as an array of 10 values, each value represents the amplitude in a specific frequency band. Then, the value in frequency band #1 of RSλ2 is subtracted from the value in frequency band #1 of RSλ1, then the values in frequency band #2 and so forth, such that the output is an array of 10 values. The output of the subtraction is a third signal RSλ3.

$$RS\lambda3 = RS\lambda1 - RS\lambda2$$

The subtraction may also be defined as S1(f)–S2(f), as S1(f) denotes the first light signal in the frequency domain and S2(f), At step 450, the third signal RSλ3 is converted from the frequency domain to the time domain. The output of the third signal RSλ3 in the time domain may be a sinusoidal signal.

FIG. 5 shows a schematic representation for a device 500 for extracting a biological parameter of a tissue of a person, according to one or more illustrative aspects of the disclosure. The device may be a wearable device, such as a watch used to monitor a biological parameter such as pulse. When the user of the wearable device moves, for example while walking, running, exercising, the movement results in noise added to the signal used to monitor the biological parameter.

The device comprises a memory module 510 for storing information used to extract the biological parameter. Such information may be a set of rules and operations used to process the signals received from the patient's body tissue.

The information may be values representing the received signals, either in the time domain or in the frequency domain.

The device comprises a sensor module 520 used to collect biological or environmental measurements in the vicinity of the device. Sensor module 520 may include an accelerometer, temperature sensor and moisture sensor. Information collected from the sensor module 520 may be used to initiate the process disclosed in FIG. 4, as the process is also used to overcome noise resulting from the user's movement.

The device comprises a processing module 530 for performing the conversions and calculations disclosed in the process of FIG. 4.

The device comprises a display unit 540 for displaying the biological parameters extracted from the light signals received from the patient's blood tissue.

Figure 6:
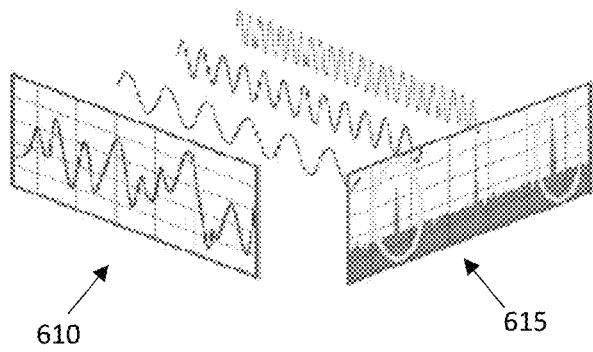
FIG. 6 shows three signals in the frequency domain that represent the method for extracting a biological parameter of a tissue of a person, according to one or more illustrative aspects of the disclosure
Figure 6:
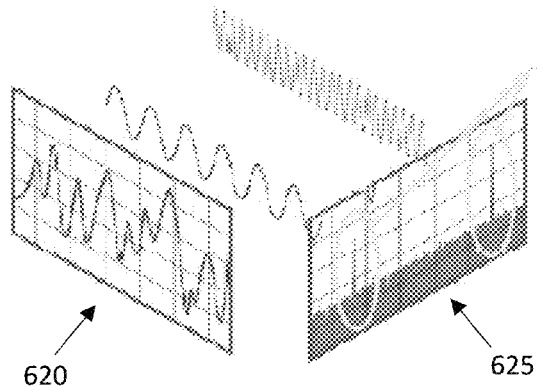
Figure 6:
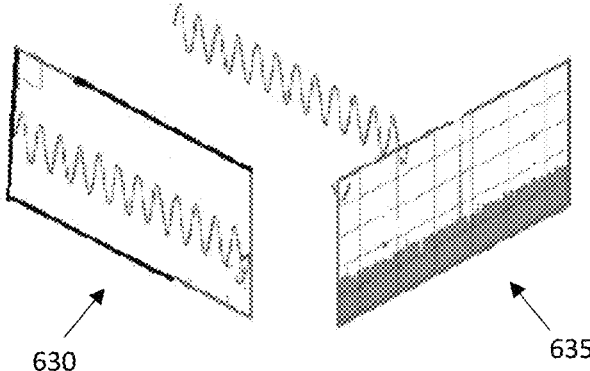

FIG. 6 shows three signals in the frequency domain that represent the method for extracting a biological parameter of a tissue of a person, according to one or more illustrative aspects of the disclosure. The first signal carries information from the blood vessel located in the tissue. The first signal is shown in the time domain 610, and in the frequency domain 615, having pulses in 3 different frequency bands. The second signal comprises substantially only noise. The noise is defined as information resulting from movement of the tissue or movement of the sensor. The second signal is shown in the time domain 620, and in the frequency domain 625, having pulses in 2 different frequency bands. The third signal is the subtraction of the second signal from the second signal. The third signal is shown in the time domain 630, and in the frequency domain 635, having pulses in one frequency band.

It is noted that the reflective measurement techniques disclosed herein are also very useful for portable as the improved SNR and AC/DC ratios they provide mitigates signals distortions that are induced in the measured signals due to movements of the body part/organ to which the sensor device is attached.

The structure of the present invention enables emission of various wavelengths and measurements of various properties. Some wavelengths are received differently from the same examined tissue. Hence, the present invention also disclosed selecting an optimal combination of angle between the light source and light detector as well as the distance between them.

As described hereinabove and shown in the associated Figs., the present invention provides a structure to enable reflective measurement configurations for measuring biological properties of an examined tissue/subject with substantially improved SNR and AC/DC ratios. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the invention.

What is claimed is:

1. A method for extracting a biological parameter of a tissue of a person, the method comprising:
   using a device comprising:
      a display;
      a light emitter configured to emit a first light signal and a second light signal towards the tissue;
      a light detector configured to collect a first received signal and a second received signal that are received from the tissue responsive to the first light signal and the second light signal respectively, and
   a component selected from the group consisting of: (i) a lens mounted to a distal end of the light emitter and configured to collimate the first and the second light signals as collimated light towards the tissue, and (ii) a reflector disposed between the light emitter and the light detector, wherein the light from the light emitter is reflected by the reflector in a direction that is laterally away from the light detector and towards the tissue:
   emitting the first light signal and the second light signal towards the tissue;
   collecting the first received signal and the second received signal that are received from the tissue responsive to the first light signal and the second light signal respectively,
      wherein emitting the first light signal comprises emitting the first light signal at a wavelength within the visible light spectrum, and
      wherein emitting the second light signal comprises configuring the second light signal such that the second light signal is inert to changes in blood vessels of the tissue towards which the second light signal is emitted, such that the second received signal carries substantially only noise;
   converting the first received signal and the second received signal to a frequency domain, represented by respective sets of values in multiple frequency bands, wherein a first set of values in multiple frequency bands represents the first received signal and a second set of values in multiple frequency bands represents the second received signal; and
   subtracting the second set of values in multiple frequency bands from the first set of values in multiple frequency bands in the frequency domain to obtain a third set of frequency bands, wherein the third set of frequency bands represents a third signal corresponding to the biological parameter of the tissue.

2. The method of claim 1, wherein the collecting is performed responsive to a delay in the emitting of the first light signal followed by the second light signal towards the tissue.

3. The method of claim 1, wherein the collecting is performed responsive to the emitting of the first light signal and the second light signal at the same time towards the tissue.

4. The method of claim 1, further comprising:
   converting the third signal from the frequency domain to the time domain.

5. The method of claim 1, further comprising displaying the biological parameter on the display.

6. The method of claim 1, wherein the emitting of the first and the second light signals is laterally in a direction away from the light detector.

7. The method of claim 1, wherein the first and the second light signals penetrate to two different depths of the tissue.

8. The method of claim 1, wherein the method is performed responsive to a movement of the person.

9. The method of claim 1, wherein the biological parameter is selected from the group comprising: a heart rate, a respiratory rate, a peripheral capillary oxygen saturation rate (SPO2), a hemoglobin level, a perspiration level, a blood pressure, a glucose level, a bilirubin level, a stroke volume and a fat level.

10. The method of claim 9, wherein the biological parameter is a heart rate or a peripheral capillary oxygen saturation rate (SPO2).

11. A device to determine a biological parameter of a tissue of a person, the device comprising:

a display;

a light emitter configured to emit a first light signal and a second light signal towards the tissue;

a light detector configured to collect a first received signal and a second received signal that are received from the tissue responsive to the first light signal and the second light signal respectively, wherein the light emitter is configured to emit the first light signal at a wavelength within the visible light spectrum, and wherein the light emitter is configured to emit the second light signal such that the second light signal is inert to changes in blood vessels of the tissue towards which the second light signal is emitted, such that the second received signal carries substantially only noise;

wherein the device is configured to convert the first received signal and the second received signal to a frequency domain, represented by respective sets of values in multiple frequency bands, wherein a first set of values in multiple frequency bands represents the first received signal and a second set of values in multiple frequency bands represents the second received signal; and wherein the device is configured to subtract the second set of values in multiple frequency bands from the first set of values in multiple frequency bands in the frequency domain to obtain a third set of frequency bands, wherein the third set of frequency bands represents a third signal corresponding to the biological parameter of the tissue, wherein the device further comprises a component selected from the group consisting of: (i) a lens mounted to a distal end of the light emitter and configured to collimate the first and the second light signals as collimated light towards the tissue, and (ii) a reflector disposed between the light emitter and the light detector, wherein the light from the light emitter is reflected by the reflector in a direction that is laterally away from the light detector and towards the tissue.

12. The device of claim 11, wherein the collimated light is in a direction laterally away from the light detector towards the tissue by an offset of a lens.

13. The device of claim 11, further comprising a memory configured to store the first and second sets of values in multiple of frequency bands.

14. The device of claim 11, wherein movement of at least one of the person and the tissue is a source of the noise.

15. The device of claim 11, wherein the device is configured to process the difference between the second set of values in multiple frequency bands and the first set of values in multiple frequency bands and to display the biological parameter on the display of the device.

16. The device of claim 11, wherein the emitting of the first and the second light signals is in a direction laterally away from the light detector.

17. The device of claim 11, wherein the light emitter is configured to emit the first and the second light signals towards the tissue such that the first and the second light signals penetrate to respective first and second depths of the tissue.

18. The device of claim 11, further comprising a differential amplifier for amplifying received analog signals received at a photo diode of the light detector, wherein an output of the differential amplifier is responsive to a movement of at least one of the person and the tissue.

19. The device of claim 11, wherein the biological parameter is selected from the group comprising: a heart rate, a respiratory rate, a peripheral capillary oxygen saturation rate (SPO2), a hemoglobin level, a perspiration level, a blood pressure, a glucose level, a bilirubin level, a stroke volume and a fat level.

20. A device to determine a biological parameter of a tissue of a person, the device comprising:

a display;

a light emitter configured to emit a first light signal and a second light signal towards the tissue;

a light detector configured to collect a first received signal and a second received signal that are received from the tissue responsive to the first light signal and the second light signal respectively, wherein the light emitter is configured to emit the first light signal at a wavelength within the visible light spectrum, and wherein the light emitter is configured to emit the second light signal such that the second light signal is inert to changes in blood vessels of the tissue towards which the second light signal is emitted, such that the second received signal carries substantially only noise;

wherein the device is configured to convert the first received signal and the second received signal to a frequency domain, represented by respective sets of values in multiple frequency bands, wherein a first set of values in multiple frequency bands represents the first received signal and a second set of values in multiple frequency bands represents the second received signal; and wherein the device is configured to subtract the second set of values in multiple frequency bands from the first set of values in multiple frequency bands in the frequency domain to obtain a third set of frequency bands, wherein the third set of frequency bands represents a third signal corresponding to the biological parameter of the tissue, wherein the device further comprises a differential amplifier for amplifying received analog signals received at a photo diode of the light detector, wherein an output of the differential amplifier is responsive to a movement of at least one of the person and the tissue.

* * * * *